United States Patent
Ciotti et al.

(10) Patent No.: US 7,797,980 B2
(45) Date of Patent: Sep. 21, 2010

(54) METHOD FOR CALIBRATING BLOOD ANALYSIS MACHINES

(75) Inventors: Alfredo Ciotti, Udine (IT); Paolo Galiano, Padua (IT); Giuseppe Ciotti, Udine (IT)

(73) Assignee: Alifax Holding S.p.A., Polverara (IT)

( * ) Notice: Subject to any disclaimer, the term of this patent is extended or adjusted under 35 U.S.C. 154(b) by 370 days.

(21) Appl. No.: 11/988,580

(22) PCT Filed: Jul. 12, 2006

(86) PCT No.: PCT/EP2006/064125
§ 371 (c)(1),
(2), (4) Date: Jan. 10, 2008

(87) PCT Pub. No.: WO2007/006791
PCT Pub. Date: Jan. 18, 2007

(65) Prior Publication Data
US 2009/0120157 A1    May 14, 2009

(30) Foreign Application Priority Data
Jul. 13, 2005    (IT) .......................... UD2005A0118

(51) Int. Cl.
G01N 15/05    (2006.01)
G01N 3/62    (2006.01)
G01N 33/49    (2006.01)
(52) U.S. Cl. ................... 73/1.02; 73/61.62; 73/61.65; 73/61.69; 73/61.71
(58) Field of Classification Search .................. 73/1.02, 73/1.82, 1.83, 61.41, 61.62, 61.63, 61.65, 73/61.69, 61.71, 61.73
See application file for complete search history.

(56) References Cited
U.S. PATENT DOCUMENTS
4,331,862 A * 5/1982 Ryan .......................... 377/29
(Continued)

FOREIGN PATENT DOCUMENTS
EP    0 887 637    12/1998
(Continued)

OTHER PUBLICATIONS
NCCLS. *Reference and Selected Procedure for the Erythrocyte Sedimentation Rate (ESR) Test; Approved Standard—Fourth Edition.* NCCLS document H2-A4 (ISBN 1-56238-424-4). 2000.

*Primary Examiner*—David A. Rogers
(74) *Attorney, Agent, or Firm*—Hamre, Schumann, Mueller & Larson, P.C.

(57) ABSTRACT

A method for calibrating machines suitable to effect an analysis of a blood sample by measuring the erythrocyte sedimentation rate (ESR) and/or aggregation of the red corpuscles, wherein the measurement is effected by exploiting the optical density kinetics obtained from the measurement of the variation in the optical density of the blood sample in an interval of time, to include measuring in which, by the same machine with which the measurement of the optical density is effected on the blood sample, a measurement is effected of the optical density of two latexes, or turbidimetric samples. Each of the two latexes has a known optical density that is reproducible, measurable and different from each other. The method also calibrates in which the difference is calculated between the values of optical density of the latexes as obtained from the measurement performed by the machine and the known values of optical density, to determine at least one correction factor usable to calibrate machine.

12 Claims, 2 Drawing Sheets

U.S. PATENT DOCUMENTS

| | | |
|---|---|---|
| 6,346,421 B1 | 2/2002 | Anderson et al. |
| 6,422,065 B1 * | 7/2002 | Shine et al. ................ 73/53.01 |
| 7,207,939 B2 * | 4/2007 | Husher ...................... 600/370 |
| 2004/0065143 A1 | 4/2004 | Husher |
| 2005/0221497 A1 * | 10/2005 | Young ......................... 436/63 |
| 2006/0023219 A1 * | 2/2006 | Meyer et al. ................ 356/432 |
| 2006/0292552 A1 * | 12/2006 | Haquette et al. ............... 435/5 |
| 2007/0003979 A1 * | 1/2007 | Worthington .............. 435/7.1 |
| 2007/0012784 A1 * | 1/2007 | Mercolino .................. 235/491 |
| 2007/0118297 A1 * | 5/2007 | Thayer ....................... 702/21 |
| 2008/0216563 A1 * | 9/2008 | Reed et al. ................. 73/61.71 |

FOREIGN PATENT DOCUMENTS

| | | |
|---|---|---|
| EP | 1 109 188 | 5/2001 |
| EP | 1 167 970 | 1/2002 |

* cited by examiner

METHOD FOR CALIBRATING BLOOD ANALYSIS MACHINES

FIELD OF THE INVENTION

The present invention concerns a method for calibrating, or setting, and controlling machines suitable to perform analyses on blood samples and used, for example, to measure the rate of sedimentation of the corpuscular part of the blood.

To be more exact, the measurement concerns the velocity of sedimentation of the erythrocytes (erythrocyte sedimentation rate, ESR) and/or the rate of aggregation of red corpuscles and is performed by exploiting the kinetics of optical density known as a syllectogram.

BACKGROUND OF THE INVENTION

In the field of blood analyses, it is known to measure the velocity of sedimentation of the corpuscular part of the blood (ESR) in order to evaluate the presence, for example, of inflammatory pathological states.

The machines and techniques used to measure ESR are known, for example as those described in the European patent application EP-A-1098188, published in the name of the present Applicant, which use optical emission means and detection means disposed on opposite sides with respect to a measuring volume.

A blood sample to be analyzed is injected into the measuring volume, and its flow is stopped suddenly, causing a characteristic kinetics of optical density of the corpusculate part present in the sample examined, which kinetics is known as syllectogram.

The optical density can be measured in units of absorbance or transmittance. Units of absorbance are determined using Lambert-Beer's law, where the value of absorbance is calculated by $A=-\log(I/I°)*L$, where $I°$ is the power of the light incident on the sample being measured, $I$ is the power of the light exiting from the sample being measured and $L$ is the length of the optical path or track, that is, the thickness of the sample.

The detection means is associated with processing means that measures said characteristic kinetics of optical density of the sample examined and calculates the ESR value or the velocity of aggregation of the red corpuscles using specific algorithms, characterized by parameters of the machine itself and its measuring characteristics.

In order to carry out the calibration of the machine, it is known to use, in parallel manner, a traditional reference method, scientifically recognized for measuring the ESR on the same blood sample, for example the Westergren method.

When the Westergren method is used as a reference, the ESR values measured are particularly sensitive to the variations in temperature of the environment where the tests are carried out. In fact, these values measured are considerably affected by the variation in temperature at which the test is carried out, as analytically described by the Stokes formula, with which the velocity of sedimentation is calculated starting from the knowledge of the rouleaux, the density of the suspension fluid, the viscosity of the liquid, etc.

It has also been proved experimentally that 3-5 Centigrade degrees of temperature variation between one test and the other on the same sample are sufficient to lose measuring accuracy to a figure of 30-50%.

For this reason, the National Committee for Clinical Laboratory Standards (NCCLS, H2-A4 Vol. 20 n° 27, page 1 "Scope ESR procedures cannot be calibrated") considers that the procedure for measuring ESR cannot be calibrated because the procedures for determining ESR are susceptible to a variety of errors.

Given that the phenomenon of erythrocyte sedimentation and aggregation, described by the syllectogram, is limited to fresh blood and is transitory, as things stand at present, it is not possible to achieve materials for the standardized calibration of this test.

Even though Westergren remains the reference method for measuring sedimentation, it should also be noted that this method is extremely laborious, it is easy to make mistakes, it presupposes that the test tube containing the blood sample is perfectly vertical during the analysis, it can be performed at most within four hours after the blood sample has been taken, and it takes a much longer time for analysis compared with an automatic machine of this type.

Some producers have made and proposed controls to be used on different measuring systems for erythrocyte sedimentation: from the glass tube for Westergren to other instruments that measure ESR. With these controls, however, different ESR values are obtained for every measuring system in which they are used. Therefore, the measurements done with different systems on the same blood sample are different from each other according to the measuring system used, while the aim of a calibration should be to supply, for the same blood sample, an aligned ESR value, that is, repeatable and in conformity with ESR values measured in different environments, irrespective of the environment in which the measuring means is used.

From the published patent application EP-A2-0887637 it is also known to use spherical particles of synthetic polymers, having an average diameter comprised between about 1 and 8 micron, a restricted distribution of particles and a low refraction index, from about 1.35 to 1.45, in order to calibrate flow cytometers, in which the size, diameter and volume of red corpuscles, reticulocytes, white corpuscles and platelets contained in a blood sample are counted and measured.

This known calibration method is valid for flow cytometers or corpuscle-counters in which, typically, the cells or other biological particles having extremely small sizes, typically between 1 and 10 micron, flow in a liquid current, so that every particle, virtually one cell at a time, passes through a detection region where, on each occasion, the physical or chemical characteristics are measured, in this case the number, diameter and/or the volume.

Such flow cytometers are not able to evaluate the variation in optical density due to the sedimentation of particles present in a blood sample in a detection zone because they are able to analyze only the chemical-physical characteristics of one particle at a time, but not to detect a phenomenon like erythrocyte sedimentation, which involves a mass of particles.

Moreover, the use of this calibration technique with individual particles does not allow, in any way, to simulate and reconstruct the development of an optical density of a blood sample to be analyzed.

One purpose of the present invention is to perfect a method that allows the calibration, setting or alignment with respect to known values of machines for analyzing blood parameters connected to the density of the blood, such as the erythrocyte sedimentation rate and/or the index of the aggregation of the red corpuscles, known in literature as the M-index, in order to obtain measurements whose overall alignment comes within a restricted range of values, for example ±10%, in a univocal, repeatable and absolute manner, without depending on the temperature or other environmental factors, and which does not have the disadvantages of the state of the art.

The Applicant has devised, tested and embodied the present invention to overcome the shortcomings of the state of the art and to obtain these and other purposes and advantages.

SUMMARY OF THE INVENTION

The present invention is set forth and characterized in the main claim, while the dependent claims describe other characteristics of the invention or variants to the main inventive idea.

In accordance with the above purpose, a method according to the present invention is used for calibrating machines that detect blood parameters connected to the density of the blood, such as the erythrocyte sedimentation rate (ESR) and/or the characteristic indexes of aggregation of the red corpuscles.

The detection is obtained by measuring and processing the variation in the optical absorbance or density, of a blood sample, caused by a sudden stoppage in the flow of the blood sample through a measuring cell or capillary. The sample is subjected to a particular analytical procedure that allows to define a particular and characteristic curve of the optical density kinetics known as a syllectogram.

The same method can also be used with other energy sources, such as for example a sound radiation or wave (at any frequency whatsoever); by suitably directing said energy sources towards the samples with known density, it is possible to measure the attenuation thereof and hence allow to calibrate the measuring system.

This analytical procedure mentioned above provides, in this specific case, to make the blood sample flow through a capillary and to suddenly interrupt the flow, in order to determine a characteristic kinetics of the corpusculate part of the sample.

According to a characteristic of the present invention, the method presupposes the use of at least two latexes, or turbidimetrical samples, or another analogous or comparable substance, and having characteristics of optical density comparable to those of the blood.

The two latexes which are used for calibration each have a known optical density that is reproducible, measurable and different from each other. Advantageously, the two values of optical density pre-selected are such that their difference is approximately equal to the maximum excursion of relative variation of optical density caused by the blood sample whose flow is suddenly interrupted.

The method according to the present invention comprises a measuring step during which a measurement is made, in sequence or separately, over time, of the optical density of each of said at least two latexes, wherein the first latex represents the value of optical density corresponding to the start of the optical density kinetics, caused by the sudden stoppage of the flow, and the second latex represents the value of optical density reached after a pre-fixed measurement time.

The measurement is obtained by injecting a certain quantity of said at least two latexes into the measuring volume, or cell, and detecting, advantageously but not necessarily in static conditions, the two different values of optical density, as if it were an analogous blood sample.

The values deriving from said measurements are for example memorized electronically, so that they are rendered always available.

When only two latexes are used, two values of turbidity are obtained, which represent relatively the beginning and the end of the kinetics. The two values are the points on which the value of the integral of optical density in the aforesaid time interval is calculated, which, in a similar manner, is calculated during a real measurement on an individual blood sample, subjected for example to an interruption in the flow, or other intervention which determines a curve that represents the absorbance reaction kinetics.

The method according to the invention also comprises a comparison step during which the values of optical density of said latexes obtained by the measurement carried out are compared with the known values of optical density of said latexes. The known concentration values of each latex have been previously determined using a standardized instrument, a photometer, which uses a determinate wave length and a particular length of the optical path, for example between 1 and 2 mm.

The comparison provides to calculate the difference between the values of optical density of the samples of latex, like a real kinetics, to allow to determine at least a correction factor, usable to calibrate the machine.

From this comparison the correction factors are obtained, to which the parameters must be regulated, for example, the machine gain, in order to perform the calibration, setting or alignment in an absolute, univocal and repeatable manner, also because, as is known, the optical density of the latexes is substantially independent of the temperature.

In general, the number of latexes of different optical density which can be used in the calibration step depends on the level of refinement to be obtained, similar to a calibration curve in which it is possible to simulate all the ranges of optical density in order to obtain all the ESR values measurable by the instrument.

The invention therefore allows to obtain a plurality of correction factors used for calibrating the machine, factors which comprise equalization values to be assigned to the various organs and elements of the machine, so as to obtain homogeneous measurements by all the instruments used to analyze the various parameters of the optical density kinetics of the blood, known as the syllectogram.

The invention is therefore suitable for all known instrumental techniques which allow to develop the optical density kinetics of the blood, or syllectogram, for example those which use flow, centrifuge, and vibration methods. All these techniques cause the destruction of the erythrocyte aggregates, or rouleaux, and when the disruptive force is suitably suspended, the optical density kinetics is analyzed, which is correlated to the formation of the rouleaux.

In this way, analyzing the same blood sample, it is possible to obtain, even with different machines but calibrated according to the invention, measurements of the ESR value characterized by great accuracy and a limited range of error in different environmental conditions such as temperature, pressure and acceleration.

Moreover, the method according to the present invention can be applied to the machine at any moment of use, for example before carrying out the measurements, during the measurements, between one group of measurements and the next, or at the end of the measurements.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 1:
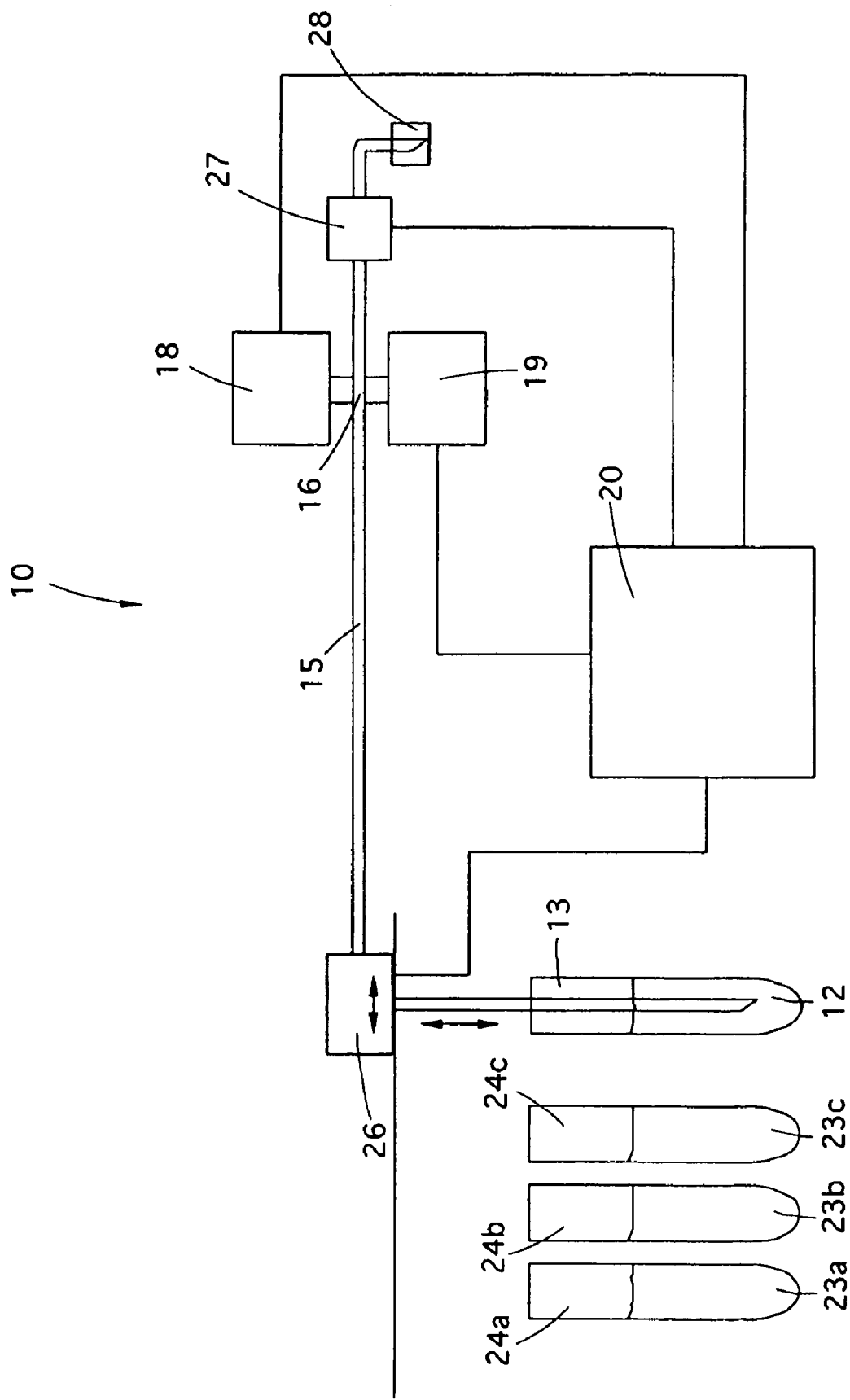
FIG. 1 is a schematic view of a machine for analyzing ESR, which implements a calibration method according to the present invention.

With reference to FIG. 1, a method according to the present invention is used for calibrating a machine 10 that detects the erythrocyte sedimentation rate (ESR) by measuring the variation in the optical density of a blood sample 12 arriving, for example, from a test tube 13.

The machine 10 comprises a tube 15 defining a measuring volume 16 into which the blood sample 12 to be analyzed is injected, and whose flow is interrupted suddenly, causing a characteristic curve of optical density. The latter is called syllectogram and is indicated by the letter "S" in FIG. 2.

It is clear that the syllectogram can be obtained using other methods known in the state of the art for measuring the erythrocyte sedimentation rate (ESR) of the blood sample 12 by means of varying the absorbance.

Figure 2:
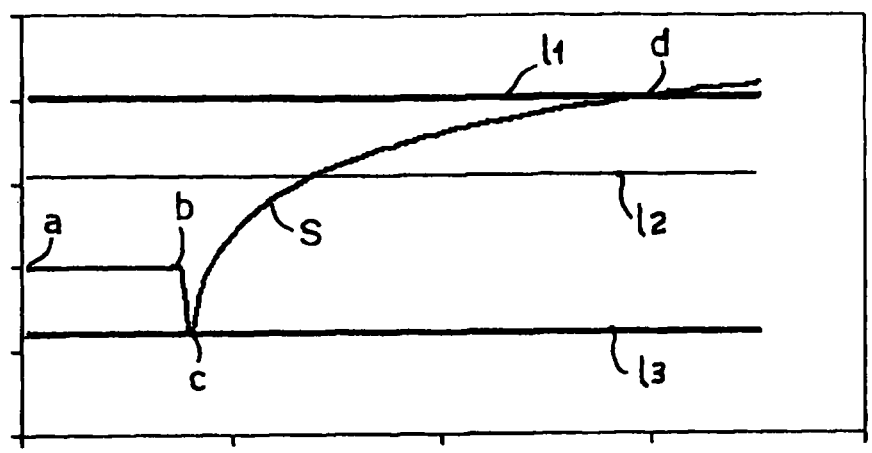
FIG. 2 shows a syllectogram in which values of optical density are shown on the y axis and values of time, in seconds, are shown on the x axis.

On the curve S in FIG. 2 a point "a" is indicated where the value of optical density of the blood sample 12 is substantially constant, while the point "b" indicated represents the instant when the flow of blood is suddenly interrupted and the optical density decreases, to a minimum value, indicated by the point "c". Afterwards, the value of optical density increases again, following its own kinetics.

The machine 10 also comprises, associated with the measuring volume 16, an emitter 18 of electromagnetic waves and a detector 19 of said waves, disposed facing each other and separated by the measuring volume 16.

The machine 10 comprises a logic unit 20 connected to the emitter 18 and to the detector 19 and able to receive the values detected by the latter relating to the variation over time of the optical density, and hence of the density of the sample in the measuring volume 16.

The logic unit 20 is also able to perform, based on the values detected, a calculation algorithm to evaluate the ESR value.

The calculation algorithm is of a known type and, in its formulation, comprises some parameters which can be regulated to allow a calibration, setting or alignment with respect to known or expected values, of the parameters of the analysis effected by the machine 10.

Before the analysis proper, the method comprises a calibration step, which provides to send into the measuring volume 16, separately and in sequence, three latexes, respectively first 23a, second 23b and third 23c, contained in corresponding containers 24a, 24b and 24c.

The latexes that can be used comprise, for example, particles of stable, inert material, such as an elastomeric natural or synthetic rubber, for example a copolymer of styrene or methylstyrene, or polyvinyl chloride or polypropylene. These particles are diluted in a liquid, stable and inert, for example water.

The three latexes 23a, 23b, 23c are chosen so that they have characteristics and properties, at least in terms of optical density, that are measurable, pre-determined, and comparable to those of the blood, and have known optical densities, different from each other and substantially independent of the temperature and pressure of the measuring environment. They may be of natural or synthetic origin.

The optical density of each of the three latexes 23a, 23b, 23c is chosen so that the optical density $l_1$ of the first latex 23a is equal to about the minimum value of optical density in a syllectogram of a blood sample (FIG. 2), that is, at the start of the optical density kinetics, point "c" in FIG. 2, whereas the optical density $l_3$ of the third latex 23c is about equal to the maximum value of optical density in said syllectogram, that is, obtained after a predetermined time point "d" in FIG. 2, and the value of optical density $l_2$ of the second latex 23b is comprised between the above minimum and maximum values in the syllectogram.

Figure 3:
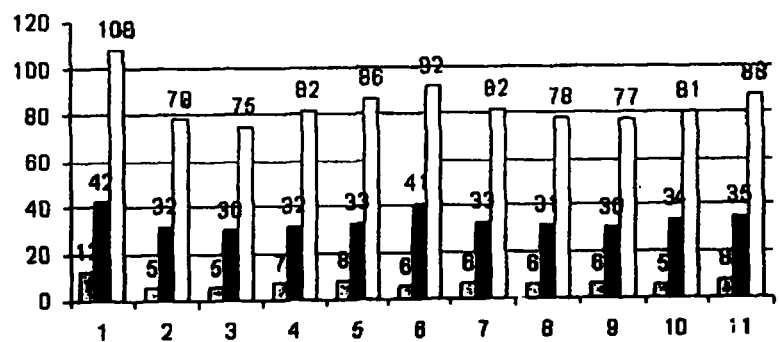
FIG. 3 shows a diagram where the values of erythrocyte sedimentation rate (ESR) are shown on the y axis, in mm/hr, measured with a plurality of measuring machines, before the calibration method according to the present invention, and where the reference number of each measuring machine is shown on the x axis.
Figure 4:
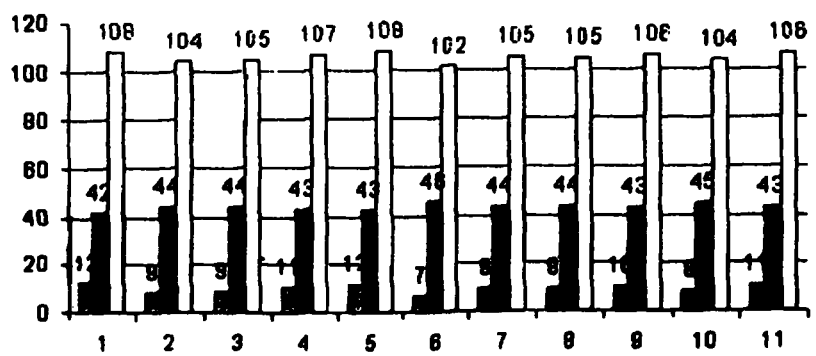
FIG. 4 shows a diagram where the values of erythrocyte sedimentation rate (ESR) are shown on the y axis, in mm/hr, measured with the measuring machines shown in FIG. 3, after the calibration method according to the present invention, and where the reference number of each measuring machine is shown on the x axis.

In FIGS. 3 and 4 the ESR values are shown calculated for the three pre-selected latexes 23a, 23b, 23c, measured by means of eleven different measuring machines, respectively before and after the calibration method according to the invention.

In correspondence with the values of optical density of the three pre-selected latexes 23a, 23b, 23c, the value of the integral of the absorbance curve is calculated, in the interval of time desired, as is done in the calculation of the integral of the curve of the syllectogram in a real kinetics.

This allows to obtain a precise calibration of any machine that measures the erythrocyte sedimentation rate ESR by achieving a syllectogram since, in practice, a real kinetics is simulated, covering the interval desired, between the minimum value, point "c", and the value at a pre-defined time, point "d".

In the embodiment shown here, the containers 24a, 24b and 24c are connected, together with the test tube 13, to the tube 15 by means of a pick-up head 26 commanded by the logic unit 20 and free to move between the containers 24a, 24b and 24c and the test tube 13.

The method comprises a first measuring step in which the logic unit 20 commands the pick-up head 26 and simultaneously a pump 27, located for example downstream of the measuring volume 16, to pick up the first latex 23a and to send it inside the measuring volume 16.

The logic unit 20 then commands the emitter 18 and the detector 19 to perform a measurement of the optical absorbance of the first latex 23a.

The measurement of the optical density of the first latex 23a is effected in a static condition of said first latex 23a, that is, with no flow, in the measuring volume 16.

The values detected are then gradually memorized in an electronic memory of the logic unit 20, so as to be able to be retrieved and compared during a second comparison step with the respective known values of optical density and advantageously memorized in an electronic memory.

Subsequently, the logic unit 20 commands the pump 27 to discharge the first latex 23a inside a tank 28.

These steps are repeated for the second 23b and the third 23c latex too, so that at the end the logic unit 20, correlating the values of optical density obtained from the machine 10 with the known values of density of the latexes 23a, 23b and 23c, finds the correction values that can be used to regulate said parameters of the calculation algorithm.

In this way, the invention allows to perform the calibration without having recourse to external apparatuses for parallel analyses with other analysis methods, and to obtain the calibration in a simple, quick and safe manner.

To be more exact, from the comparison between FIG. 3, where the y axis shows the values measured of the erythrocyte sedimentation rate ESR obtained from the latexes 23a, 23b, 23c, in mm/hr, by eleven different measuring machines, listed on the y axis, before calibration with the latexes according to the invention, and FIG. 4, where the values measured of the erythrocyte sedimentation rate ESR for said latexes 23a, 23b, 23c, in mm/hr, are shown on the y axis, with said eleven different measuring machines grouped together on the y axis, after calibration with the latexes according to the invention, it is possible to observe the clear improvement in the analytical response, in terms of alignment with respect to the value measured by the machine identified by the number 1 in FIG. 3 and FIG. 4, and in terms of precision and reliability of the measurement of the erythrocyte sedimentation rate ESR, thanks to the calibration according to the present invention.

The invention also allows to indirectly verify the correct functioning of the mixing members, identification members, pick-up members, pumping members, calculation members, members for printing the results and for sending said measurements through information means, such as serial communication lines, also to other information means in order to memorize the calibration data, also on subsequent days, in order to control the development thereof.

The calibration values themselves can advantageously be memorized in the machine 10 in order to verify the behavior thereof in the following days of use.

After the calibration and comparison steps, the logic unit 20 commands the pick-up head 26 and the pump 27 to take in the blood contained in the test tube 13 and dispose it in the measuring volume 16, so as to be able to perform the analysis thereon by means of the emitter 18 and the detector 19 when the machine 10 is completely calibrated.

It is clear that modifications and/or additions of parts may be made to the method as described heretofore, without departing from the scope of the present invention.

For example, it may be provided to associate, at least with the measuring volume 16, a conditioning device able to keep the temperature of the sample constant.

It may also be provided to make as many measuring volumes as there are calibration latexes 23a, 23b, 23c and another measuring volume for the blood sample 12.

It is also clear that, although the present invention has been described with reference to some specific examples, a person of skill in the art shall certainly be able to achieve many other equivalent forms of method for calibrating machines for analyzing parameters of the blood connected to the density of blood, such as the erythrocyte sedimentation rate and/or rate of aggregation of the red corpuscles, having the characteristics as set forth in the claims and hence all coming within the field of protection defined thereby.

The invention claimed is:

1. A method for calibrating machines to effect an analysis of a blood sample by measuring erythrocyte sedimentation rate (ESR) and/or aggregation of red corpuscles, wherein measurement is performed by exploiting optical density kinetics obtained from measurement of variation in optical density of said blood sample in an interval of time, comprising a measuring step in which, the same machine with which the measurement of the optical density is performed on said blood sample, wherein a first measurement is performed of the optical density of a first of at least two latexes, or turbidimetric samples, having a known optical density that is reproducible and measurable, and wherein a second measurement is performed of the optical density of a second of said at least two latexes having a known optical density that is reproducible, measurable and different from the optical density of said first latex, and a calibration step, in which the difference is calculated between the values of optical density of at least said first and second of said at least two latexes as obtained from the measurements performed by the machine and the known values of optical density, to determine at least one correction factor usable to calibrate said machine.

2. The method as in claim 1, wherein said optical density kinetics is obtained from a sudden stoppage of flow of said blood sample through a measuring cell.

3. The method as in claim 1, wherein said correction factor is a value proportional to gain to be assigned to the machine.

4. The method as in claim 1, wherein said latexes are of natural or synthetic origin.

5. The method as in claim 1 wherein the optical densities of said latexes or of analogous or comparable substances, is substantially independent with respect to temperature and pressure.

6. The method as in claim 1, wherein during said measuring step, said latexes are analyzed separately in a single calibration process, in order to obtain relative different values of optical density.

7. The method as in claim 1, wherein during said measuring step, said latexes are analyzed in sequence in a single calibration process, in order to obtain relative different values of optical density.

8. The method as in claim 1, wherein during said measuring step, the values measured are memorized electronically.

9. The method as in claim 1, wherein said method is independent of environmental conditions where the machine is located.

10. The method as in claim 1, wherein the values of optical density of said at least two latexes comprise a minimum and maximum range of variation in optical density caused by said blood sample which is made to flow through a measuring capillary and which flow is suddenly stopped, defining a characteristic curve of optical density of the blood sample.

11. The method as in claim 1, wherein the optical density measured for the first of said two latexes represents the optical density of the beginning of the optical density kinetics, caused by a sudden stoppage of the flow of said blood sample, and the optical density measured for the second of said two latexes represents the optical density after a pre-fixed measuring time.

12. The method as in claim 1, wherein during said measuring step, said optical density is measured by emitting from an emitter an electromagnetic wave or a sound wave and by detecting said electromagnetic wave or said sound wave by a detector.

* * * * *